United States Patent [19]

Carrier et al.

[11] Patent Number: 4,707,685

[45] Date of Patent: Nov. 17, 1987

[54] DEVICE FOR DETECTING THE ONSET OF PARTURITION OF A PREGNANT ANIMAL

[75] Inventors: Denis Carrier, C.P. 186, Rang Petit Nedelec, Notre-Dame-Du-Nord, Quebec, Canada, J0Z 3B0; Andre Saintonge, Judge, Canada

[73] Assignee: Denis Carrier, Notre-Dame-Du-Nord, Canada

[21] Appl. No.: 890,542

[22] Filed: Jul. 30, 1986

[30] Foreign Application Priority Data

Nov. 13, 1985 [CA] Canada ................................. 495253

[51] Int. Cl.$^4$ ...................... G08B 23/00; A61B 5/10
[52] U.S. Cl. ................................. 340/573; 128/775; 340/539
[58] Field of Search ............... 340/573, 539; 128/775, 128/778, 361

[56] References Cited

U.S. PATENT DOCUMENTS

| 4,028,687 | 6/1977 | Hamaguchi et al. | 340/573 X |
| 4,055,839 | 10/1977 | Skeggs | 340/573 X |
| 4,147,160 | 4/1979 | Aranow et al. | 128/775 |
| 4,217,575 | 8/1980 | Lorette | 340/573 |
| 4,232,686 | 11/1980 | Kammlade, Jr. | 128/775 |
| 4,319,583 | 3/1982 | Ingle | 128/775 |

Primary Examiner—Glen R. Swann, III
Assistant Examiner—Thomas J. Mullen, Jr.
Attorney, Agent, or Firm—Robic, Robic & Associates

[57] ABSTRACT

A device for detecting the onset of parturition of a pregnant animal which comprises a thin, electrically conducting wire passing through the left and right sides of the animal's vulva region so that a middle portion of the wire lies across the vaginal orifice of the animal. Two stoppers are fixedly mounted on the two end portions of the thin wire and positioned so as to cause, upon separation of the left and right sides of the animal's vulva region at the onset of parturition of the animal, a tensile stress into a central portion of the thin, electrically conducting wire defined between the two stoppers and including the wire middle portion lying across the vaginal orifice, which tensile stress breaking this central portion. A switching unit connected to the two end portions of the thin, electrically conducting wire detects breaking of the wire central portion to thereby detect the onset of parturition of the animal. Such a detecting device may be used within an alert device for producing an alarm upon detection of the onset of parturition of the animal.

19 Claims, 10 Drawing Figures

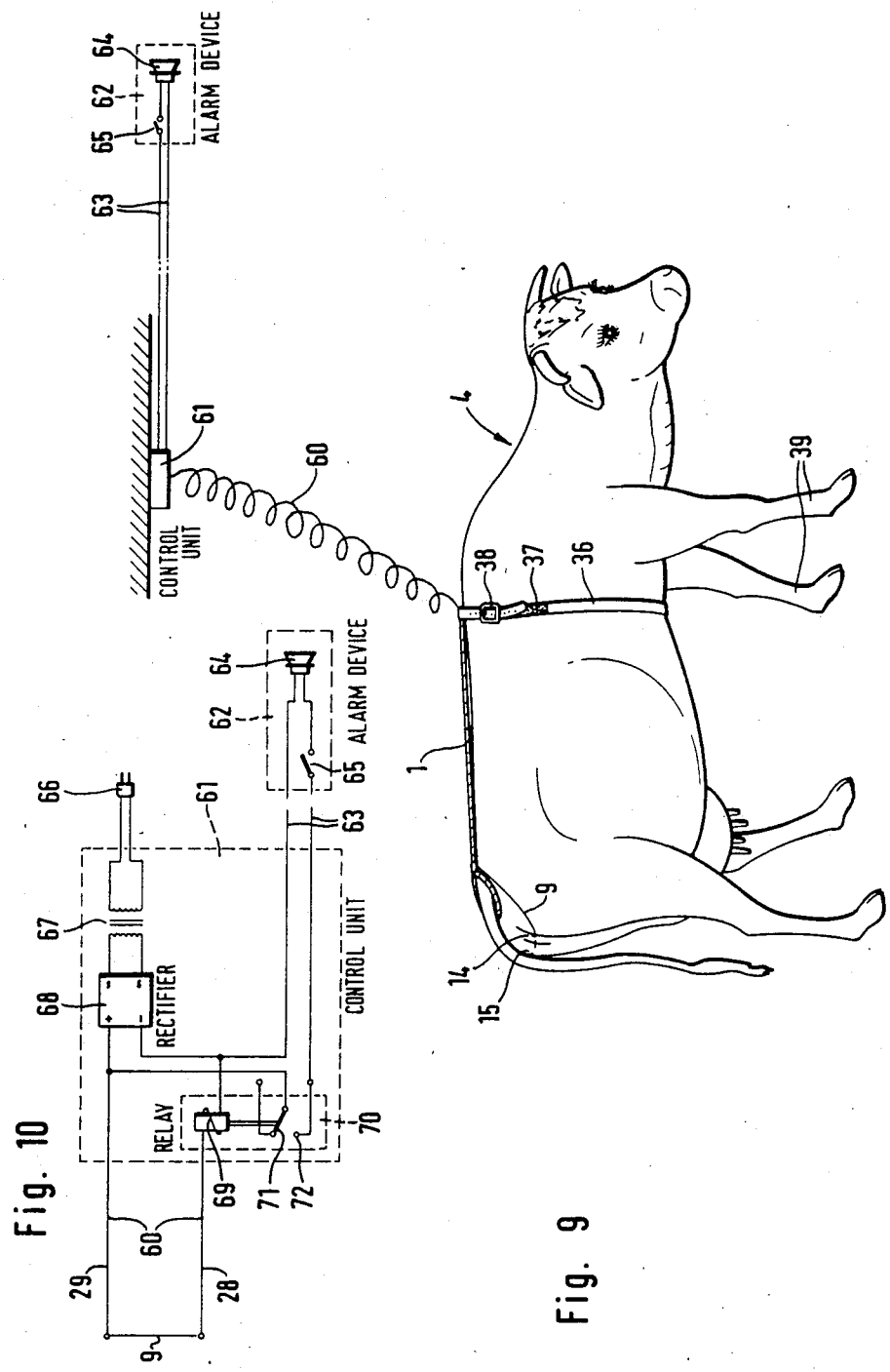

DEVICE FOR DETECTING THE ONSET OF PARTURITION OF A PREGNANT ANIMAL

The present invention relates to a device for automatically detecting the onset of parturition of a pregnant animal, and a parturition alert device using such a detecting device.

It is well known that animals such as cows, mares, pigs, etc... often need help when bringing forth young in order to assure safe birth. However, as in most of the cases the attendant cannot be continuously present in the proximity of a pre-parturient animal for assistance upon delivery of this animal, in particular during the night when he sleeps and when most of the births occur, the onset of parturition should be automatically detected and an alert remotely given to the attendant so that he can assist delivery of the pregnant animal.

U.S. Pat. No. 4,147,160 (ARANOW et al) issued on Apr. 3, 1979, describes an alert device for producing an alarm upon foaling of a mare. Such an alert device comprises a first coupling element attached on one of the two opposite exterior sides of the mare's vulva and another coupling element attached to the second exterior side of the vulva, these two elements being designed to be coupled together. Upon separation of the two opposite sides of the vulva caused by foaling of the mare, the second element is uncoupled from the first one. A switch of the first element then activates a radio-transmitter also included in the first element so that a signal is transmitted through the air to operate a remote alarm. The first and second elements are attached on the two opposite sides of the vulva by sutures or other suitable securement means. A first drawback of such an alert device is its relatively important volume. Detachment of the first and/or second elements from the skin of the mare is consequently possible if the animal tries to get rid of the alert device for any reason for example due to itching caused by the sutures. The mare then rubs the alert device against any surrounding wall or other structure. Another disadvantage of this alert device is that the transmitter is located at a position where it is subjected to humidity and possible crushing. The housing of the first coupling element enclosing the transmitter must consequently be impervious to humidity in order to ensure good operation. A third disadvantage is that the transmitter must have at the same time a relatively high radiation power in order to enable operation of a remote alarm and a small volume in order to decrease at the minimum the volume of the first coupling element for the reasons exposed hereinabove, these two characteristics for the transmitter being of course incompatible.

The apparatus for remotely indicating the onset of parturition of an animal described in U.S. Pat. No. 4,232,686 (KAMMLADE, Jr) issued on Nov. 11, 1980, comprises a rupturable assembly adapted to be mounted across the vaginal orifice of the animal. The rupturable assembly has a preferred rupture line along which the assembly ruptures when the vaginal orifice distends during the onset of parturition. A permanent magnet positioned on a first side of the rupture line holds a switch positioned on the other side of this line open while the rupturable assembly is unruptured in order to prevent energization of a transmitter. Upon rupture of the assembly, the magnet is separated from the switch whereby the switch closes to energize the transmitter which transmits a radio signal indicative of the onset of parturition of the animal. A first drawback of such an indication apparatus is that a malfunction may be caused by rubbing the rupturable assembly on a magnetic material, for example a steel tube, which magnetic material may cause dispersion of the magnetic flux produced by the magnet. Another disadvantage of this apparatus is the position of the transmitter on the side of the animal. Due to such a position of the transmitter, it is difficult to securely attach the same to the animal who can easily detach it by rubbing the transmitter on any surrounding wall or other structure. Moreover, the animal may lie down on his side to deliver, thereby subjecting the transmitter to very difficult operating conditions. A further disadvantage of such an apparatus is that the evacuation of the amniotic liquid may cause rupture of the rupturable assembly to thereby cause separation of the magnet and the switch to produce an anticipated alarm.

The birth detector of U.S. Pat. No. 4,319 583 (INGLE) issued on Mar. 16, 1982, is provided with a transmitter attached to the skin of the pregnant animal proximate one side of the animal's vulva. This transmitter utilizes a reed relay switch to sense the proximity of a permanent magnet attached on the opposite side of the vulva. As the vulva dilates at the time of delivery of the animal, the magnet is moved out of the magnetic field sensing area of the reed switch, turning on the transmitter whose transmissions are received by a remote receiver monitored by an attendant. The transmitter and the magnet are held in place on the animal by an adhesive coated or sutured vinyl holding pad. Another embodiment of this birth detector uses a wire lying across the vaginal orifice of the animal, which wire upon dilatation of the animal's vulva disconnects a jack to activate a mechanical switch which energizes the transmitter. This wire has therefore a mechanical function only. Again, this birth detector has the disadvantage of having a transmitter located at a position where it is subjected to humidity. In the stanby mode of the transmitter, the mechanical or reed relay switch is closed so that a non negligible current is supplied to a low-value resistor. Moreover, the coil antenna of the transmitter has also a lower radiation compared with a straight antenna having a same length, so that more electric power is required. A battery having a suitable capacity must therefore be provided to meet these electric energy requirements, which battery causes an augmentation of the volume of the transmitter and the drawbacks inherent to such an augmentation of volume discussed hereinabove with respect to U.S. Pat. No. 4,147,160 (ARANOW et al). Another disadvantage of this birth detector is that attachment of the transmitter and the magnet through glue may fail to suitably secure the same to the animal. The other solution which consists in suturing the vinyl holding pad is difficult to carry out because the skin in the region of the vulva of a pre-parturient animal is very soft. This latter solution may also be rendered difficult to carry out by the hair of the animal. Moreover, such suturing is hardly practicable in the environment where it has to be executed.

An object of the present invention is therefore to provide a device for detecting the onset of parturition of a pregnant animal as well as a parturition alert device using such a detecting device which eliminate the above discussed drawbacks and disadvantages inherent to the prior art.

In accordance with the present invention, there is provided a device for detecting the onset of parturition of a pregnant animal, comprising:

a thin, electrically conducting wire passing through a first perforation point made through the skin of the animal on the left side of the animal's vulva region, and also passing through a second perforation point made through the skin of the animal on the right side of the animal's vulva region, the thin, electrically conducting wire comprising a middle wire portion defined between said first and second perforation points and lying substantially across the vaginal orifice of the animal, the thin wire also comprising a first end, a second end, a first end portion defined between said first end and said first perforation point, and a second end portion defined between said second end and said second perforation point;

first stopper means fixedly mounted on the first end portion of the thin wire close to the first perforation point, and second stopper means fixedly mounted on the second end portion of the thin wire close to the second perforation point, said first and second stopper means defining a central portion of the thin, electrically conducting wire, which central portion includes said middle wire portion, and said first and second stopper means causing, upon separation of the left and right sides of the animal's vulva region at the onset of parturition of the animal, a tensile stress into said central portion of the thin, electrically conducting wire in order to break said thin wire central portion; and means for detecting breaking of said central portion of the thin, electrically conducting wire to thereby detect the onset of parturition of the animal.

In accordance with the present invention, there is also provided a parturition alert device comprising:

the above described parturition detecting device according to the invention; and means for producing an alarm indicating the onset of parturition of the animal in response to detection of breaking of said central portion of the thin, electrically conducting wire by the breaking detecting means of the parturition detecting device.

The objects, advantages and other features of the present invention will become more apparent upon reading of the following non-restrictive description of preferred embodiments thereof, given with reference to the accompanying drawings, in which:

FIGS. 9 and 10 represent a second embodiment of the parturition alert device in accordance with the present invention.

Figure 1:
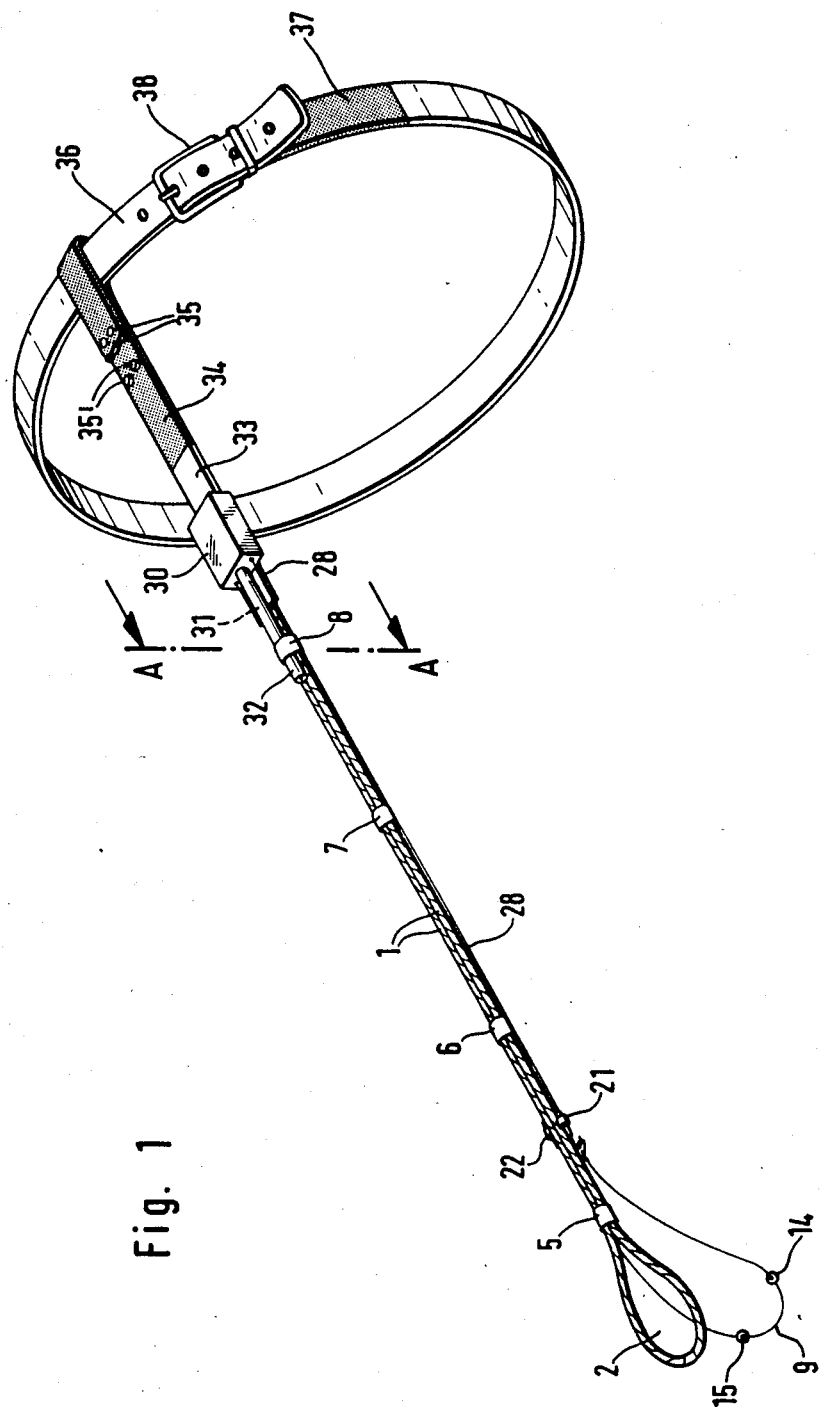
FIG. 1 represents in part a first embodiment of a parturition alert device according to the present invention adapted to be mounted, for the purpose of exemplification only, on a cow.

As illustrated on FIG. 1 of the attached drawings, the alert device comprises first strap means including a nylon rope 1 bent to form a loop defining an oblong hole 2 through which the tail of the animal is passed. This is better illustrated on FIG. 2 where the tail 3 of a cow 4 is passed through the oblong hole 2 formed by the rope 1 of the first strap means. As shown on FIG. 1, the two portions of the bent nylon rope 1 are retained together through fasteners 5 to 8.

Alternatively, the nylon rope 1 may be simple instead of being double as illustrated in FIG. 1, between the fastener 5 and the opposite end of the first strap means.

The alert device also comprises a detector of the onset of parturition of the cow including an electrically conducting wire 9 having a small diameter, for example a wire having a #30 gauge. A small diameter is selected for the wire 9 so that the same can be easily broken at the onset of parturition of the cow 4 as will be seen in greater details hereinafter.

Figure 3:
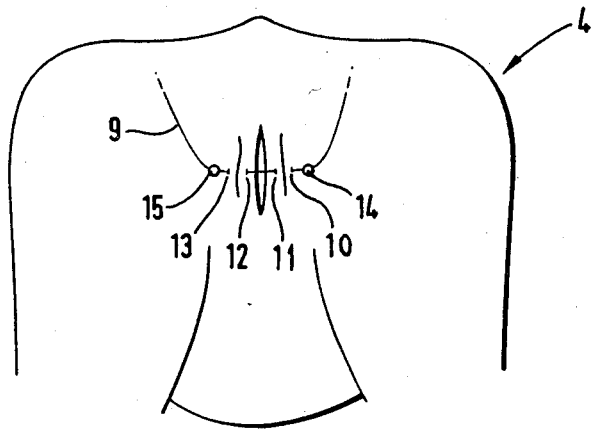
FIG. 3 illustrates the thin, electrically conducting wire passing through the left and right sides of the cow's vulva region and having two stoppers fixedly mounted thereon, which wire is also illustrated on FIGS. 1 and 2.

As illustrated on FIG. 3, the wire 9 is passed through a perforation point made through the skin of the cow on the right side of the cow's vulva region (from reference 10 to reference 11 in FIG. 3), and is also passed through another perforation point made through the skin of the cow on the left side of the cow's vulva region (from reference 12 to reference 13 in FIG. 3). The wire 9 is thereby fixedly mounted on the cow who cannot get rid of it by rubbing it against a surrounding wall or other structure. It can be appreciated that the positions of the two perforations points are selected approximate the vaginal orifice of the cow so that a middle portion of the wire 9 defined between the two perforation points lies across the vaginal orifice of the cow 4. Of course, the wire 9 is preferably externally insulated to prevent electrical conduction through the cow 4.

In order to pass the wire 9 through the left and right sides of the cow's vulva region, this wire 9 can be inserted into the eye of a needle. The needle is then passed through a pinch of skin on the right side of the cow's vulva region and thereafter through another pinch of skin on the left side of the cow's vulva region. It should be noted here that the use of a conventional needle of a relatively low diameter is enabled due to the small diameter of the wire 9.

The wire 9 comprises a first end portion defined between the right perforation point and the corresponding end of the wire 9 and on which is fixedly mounted a first stopper 14 close to the right perforation point, and a second end portion defined between the left perforation point and the corresponding end of the wire 9 and on which is mounted a second stopper 15 close to the left perforation point.

Figure 4:
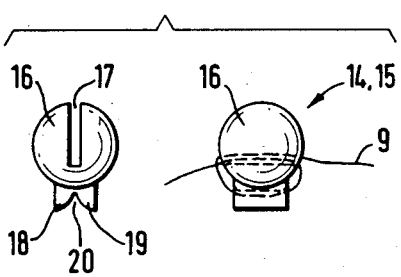
FIG. 4 shows the structure of the two stoppers which are fixedly mounted on the thin, electrically conducting wire.

Each stopper 14 or 15 is formed, as illustrated on FIG. 4 by a lead split ball 16 including a groove 17 and two ridges 18 and 19 forming another groove 20 therebetween. In order to mount each stopper 14 or 15 on the wire 9, this wire is passed a first time through the groove 17. It is then wrapped into the grooves 20 and 17. Last of all, each lead stopper 14 or 15 is crushed by means of pliers to become fixedly mounted on the wire.

Of course, the two lead stoppers 14 and 15 must be mounted on the wire 9 with a spacing therebetween sufficient to allow the evacuation of the amniotic liquid, if necessary.

As the wire 9 is mounted across the vaginal orifice as explained hereinabove, through the stoppers 14 and 15, and as the wire 9 is of a small diameter and consequently relatively easy to break, one can appreciate that upon the onset of parturition of the cow 4, separation of the left and right sides of the cow's vulva region will cause a tensile stress in the wire 9 which breaks the central portion of the wire 9 defined between the stoppers 14 and 15, thereby providing detection of the onset of parturition. Separation of the left and right sides of the vulva region of the animal occurs significantly only at the time of birth, particularly during the expulsion of the fetus. It is therefore at that time that the central portion of the wire 9 is broken.

The dimensions of the lead stoppers 14 and 15 should be selected to meet at the same time with the following two requirements: the leads stoppers 14 and 15 should have dimensions as reduced as possible to prevent the cow to get rid of the wire 9 by rubbing these stoppers on a surrounding wall or other structure, but should also have sufficient dimensions to prevent cutting by the wire 9 of the two stoppers 14 and 15 upon application of tensile stress on the central portion of the thin, electrically conducting wire 9.

It should be pointed out that mounting of the wire 9 on the animal with the help of a needle causes no problem. Indeed, the vulva region of an animal is very soft and almost unsensitive during the period preceding parturition of this animal. Moreover, during this period, the animal produces hormones which provide protection against infection caused by the mounting of the wire 9 on the animal.

Figure 5:
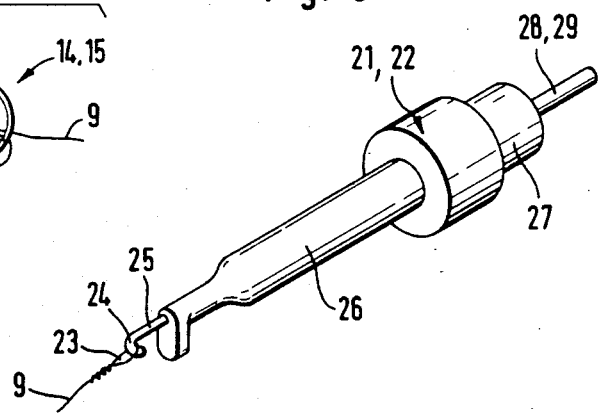
FIG. 5 is an enlarged view of one of two clips shown on FIG. 1 and provided for connection to the thin, electrically conducting wire.

As illustrated on FIG. 1, each end of the wire 9 is attached to a corresponding clip 21 or 22 provided on each side of the bent nylon rope 1. As better shown on FIG. 5, a loop 23 is formed at each end of the wire 9, which loop is attached to a hook 24 of the corresponding clip 21 or 22. Such a clip 21 or 22 of a well-known type comprises an electrically conducting rod 25 having an end forming the hook 24, which rod 25 is slidably mounted in the body 26 of the clip. An end part 27 is also slidably mounted with respect to the body 26, and a spring enclosed within the body 26 and/or the part 27 is interposed between these body 26 and part 27. By pressing this spring, the part 27 can be moved longitudinally towards the interior of the body 26 whereby the rod 25 and hook 24 are also longitudinally moved within the body 26 to allow insertion of the loop 23 into the hook 24. By releasing the spring, the rod 25 is re-inserted into the body 26 and the loop 23 is secured to the clip 21 or 22 through the hook 24.

As can be appreciated, after the central portion of the wire between the stoppers 14 and 15 has been broken, this central portion can be easily removed from the cow only by pulling the two lead stoppers 14 and 15. Thereafter, the broken, thin electrically conducting wire 9 can be detached through the clips 21 and 22 and thrown away with the two stoppers. Another wire 9 can then be used in combination with new lead stoppers 14 and 15 for another parturition detection.

Each clip 21 or 22 has its rod 25 and consequently its hook 24 electrically connected with an electric wire 28 or 29 disposed along the nylon rope 1 forming the first strap means. These wires 28 and 29 are attached through the fasteners 6, 7 and 8 as the rope 1, and are electrically connected to a transmitter 30 forming part of the alert device, as illustrated on FIG. 1, so that the two end portions of the wire 9 are connected to this transmitter 30 through the loops 23, the hooks 24, the rods 25 and the wires 28 and 29. FIG. 1 shows only one of the wires 28 and 29, namely the wire 28 for the purpose of simplification of the drawings.

The transmitter 30 comprises a wire antenna 31 having a suitable length and surrounded by a tube 32 made of plastic material. This tube 32 is provided to avoid an exaggerated load on the antenna 31, by contact of this antenna 31 with a wet litter or other wet substances, which would cause a reduction in radiation.

The free end of the antenna 31 may also be associated with an arrangement attached to the rope 1 through the fastener 8 and designed to distance the free end of the antenna from the animal so as to obtain a better radiation.

Figure 6:
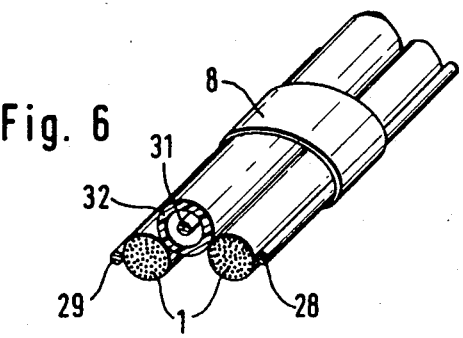
FIG. 6 is a cross-section of the alert device taken along axis A—A of FIG. 1.

FIG. 6 shows a cross-section taken along the axis A—A of FIG. 1. More particularly, FIG. 6 illustrates the two portions of the rope 1, the two wires 28 and 29, the antenna 31 and the plastic tube 32 attached together through the fastener 8.

The two ends of the nylon rope 1 are attached to a strap 33 on which is secured the transmitter 30 as can be seen on FIG. 1. The transmitter is therefore positioned to be out of reach by the cow and almost not subjected to humidity. Moreover, the volume of the transmitter at this position is not a limiting factor.

The strap 33 includes an elastic end portion 34 which forms a loop in which is inserted second strap means. Snaps 35 are advantageously provided to form the loop of the elastic strap portion 34 in order to facilitate mounting and removal of the first strap means. A plurality of pairs of snap male portions such as 35' may be provided to adjust the length of the first strap means to the dimensions of the cow 4. The elastic portion 34 is of course designed to allow cambering of the back of the cow upon urinating.

In accordance with an alternative embodiment, the snaps 35 may be replaced by a first large safety-pin to attach the elastic end portion 34 in order to form the loop surrounding the second strap means. A second large safety-pin may also be provided to attach the elastic end portion 34 to the second strap means in order to prevent sliding of the first strap means on the second strap means.

The second strap means are formed by a strap 36 including an elastic strap portion 37. This elastic portion 37 produces a constant force around the body of the cow 4 while making the second strap means comfortable to the cow. The constant force made by the elastic portion 37 also prevents rotation of the second strap means 36 about the animal chest. These second strap means also comprise a buckle 38 to attach the two ends of the strap 36 in order to allow mounting of the same around the body of the cow 4, just behind the two front legs 39 of this cow 4, as shown on FIG. 2. Of course, the buckle 38 is of a conventional adjustable type so that the length of the strap 36 can be adapted to the size of the cow 4.

Figure 2:
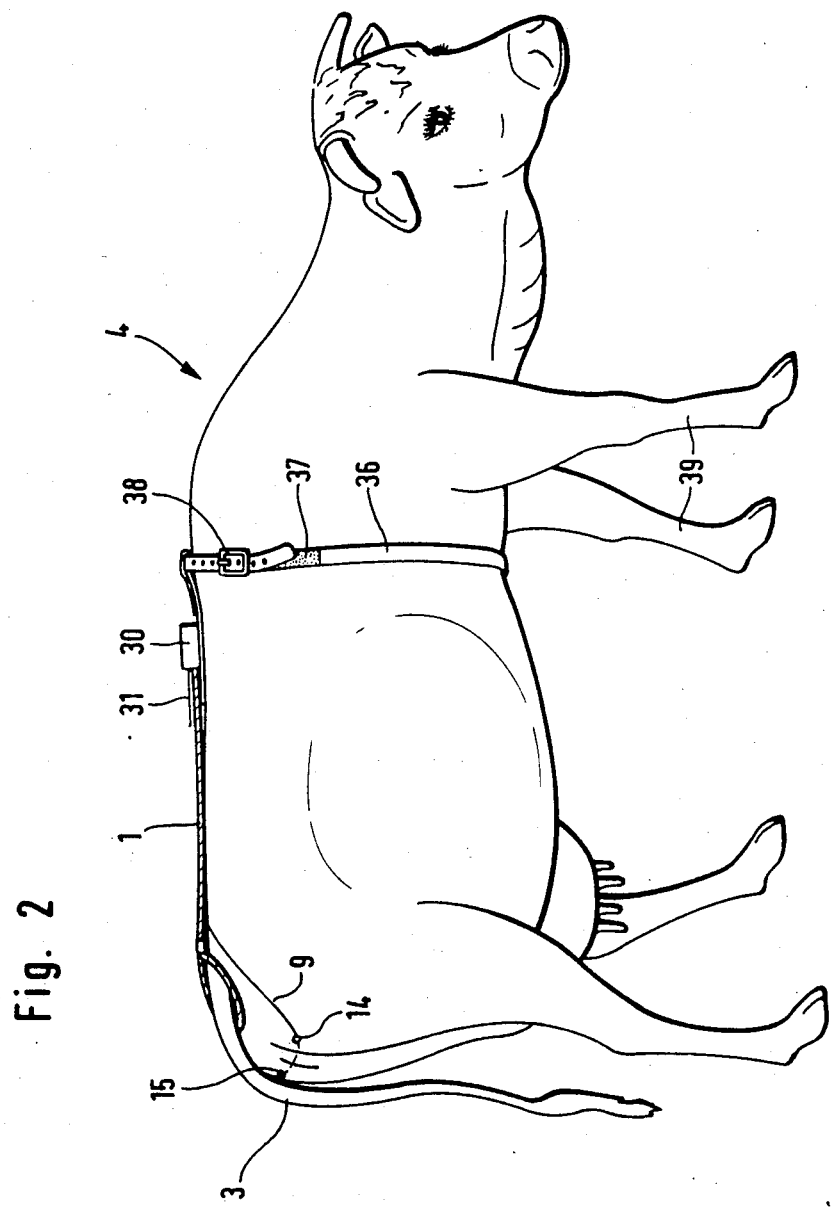
FIG. 2 shows the alert device of FIG. 1 mounted on a cow.
Figure 7:
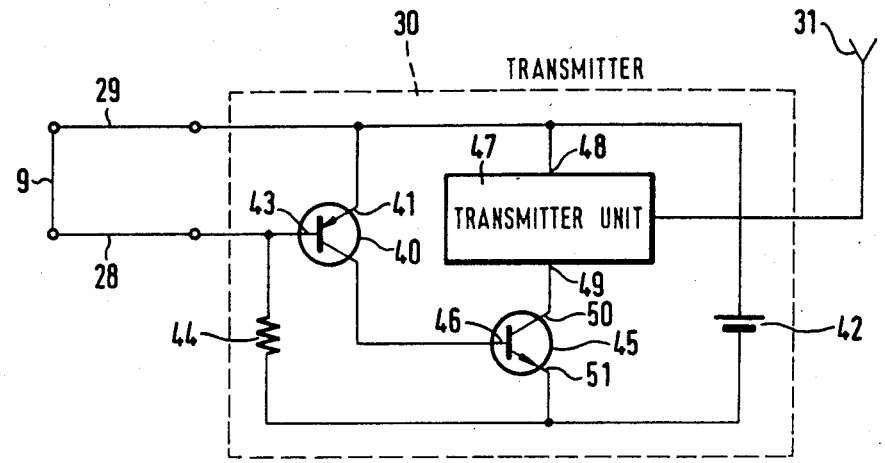
FIG. 7 is the circuit of a transmitter of the alert device of FIG. 1.

FIG. 7 represents the circuit of the transmitter 30 of FIGS. 1 and 2. This transmitter 30 comprises a PNP transistor 40 having an emitter electrode 41 connected to a positive voltage supplied by a DC (direct current) supply source 42 and to a first end of the thin wire 9 of FIG. 1 through the wire 29, and a base electrode 43 connected to the second end of the thin wire 9 through the wire 28. The thin, electrically conducting wire 9 of FIG. 1 therefore interconnects the emitter and base electrodes of the transistor 40 to turn off the same. Upon breaking of the thin wire 9 caused by parturition of the cow, the emitter and base electrodes 41 and 43 of the transistor 40 are disconnected whereby the transistor 40 is turned on as a base current can then be established through the resistor 44 interconnecting the base electrode 43 with the ground of the source 42. The transistor 40 of the transmitter 30 is therefore a part of the parturition detector of the alert device as it detects breaking of the thin, electrically conducting wire 9.

It can be appreciated here that the thin, electrically conducting wire 9 has not a mechanical function, as in the case of the corresponding wire of the above discussed U.S. Pat. No. 4,319,583 (INGLE), but has an electrical function (interconnection and disconnection of the emitter and base electrodes 41 and 43 of the transistor 40).

When the transistor 40 is turned on, it supplies a base current to the base electrode 46 of a NPN transistor 45 to turn on the latter. A transmitter unit 47 is then supplied by the source 42 through its supply inputs 48 and 49, and the collector and emitter electrodes 50 and 51 of the transistor 45, which transmitter unit 47 emits a signal through the air by means of the antenna 31 also shown on FIG. 1.

It should be pointed out that as long as the thin, electrically conducting wire 9 is not broken, the source 42 only supplies a current through the high value resistor 44 so as to reduce stanby consumption of the transmitter 30. This presents an important advantage when the source 42 is constituted by for example a 9-volt battery easily available on the market.

Figure 8:
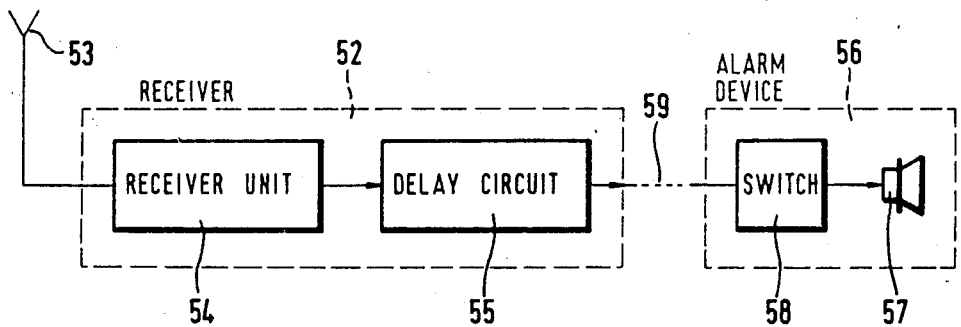
FIG. 8 is the circuit of a receiver associated with the transmitter of FIG. 7, and of an alarm device associated with this receiver.

FIG. 8 is a block diagram of a receiver 52 of the alert device, which receiver 52 is associated with the transmitter 30. The receiver 52 is provided with an antenna 53 for detecting the signal emitted through the antenna 31 of the transmitter 30, with a receiver unit 54 and with a delay circuit 55. Upon detection by the antenna 53 of the signal emitted by the transmitter 30 after the thin, electrically conducting wire 9 has been broken, the receiver unit 54 activates through the delay circuit 55 an alarm device 56 comprising a buzzer 57 and a switch 58. The delay circuit 55 is provided to delay energization of the alarm 56 by the receiver unit 54 to prevent activation of this alarm device 56 by a parasital signal of short duration detected through the antenna 53 of the receiver unit 54. The delay introduced by the circuit 55 is of for example 12 seconds, which delay is sufficient to prevent activation of the alarm device 56 by the usual parasital signals which can be detected through the antenna 53. Moreover, such a delay of 12 seconds is very short compared with the time required for cows to bring forth young.

As can be seen on FIG. 8, the receiver unit 54 energizes through the delay circuit 55 the buzzer 57 through the switch 58. This switch 58 is provided to allow the attendant to stop emission of sounds through the buzzer 57 after he has acknowledged the alarm indicating that the cow is bringing forth.

When the transmitter unit 47 emits with a sufficient power through its antenna 31 the signal indicating breaking of the wire 9, the receiver 52 may be positioned remote from the transmitter 30, for example in the house of a farm while the transmitter 30 is mounted on the cow 4 in the stable of the farm. In this case, the receiver 52 can also be carried by the attendant provided that the transmission distance limit of the transmitter-receiver tandem is respected.

When the signal is emitted from the antenna 31 with a low power, the receiver 52 is located in the stable in the proximity of the transmitter 30 while the alarm device 56 is positioned, for example, in the house of the farm. In this case, a cable 59 of substantial length interconnects the receiver 52 with the alarm device 56 from the stable to the house. This latter embodiment is particularly useful in the case of an untied cow who can move in the stable. The cable 59 may of course be replaced by a transmitter-receiver tandem in which the receiver is located in the house of the farm or carried by the attendant.

It is evident that a plurality of transmitters such as 30 associated with a plurality of cows can be used simultaneously with a single receiver 52. At the onset of parturition of any one of the cows, the associated transmitter 30 transmits a signal to the receiver unit 54 through the antennas 31 and 53 in order to activate the alarm device 56 which indicates the onset of parturition of one of the cows.

Of course, the transmitter 30 may be designed to emit radio waves, microwaves, infrared energy or ultrasounds. The receiver 52 must also be designed to receive the type of emission used by the transmitter 30.

Another embodiment of the alert device according to the present invention is shown on FIGS. 9 and 10 of the attached drawings and adapted for a cow tied up in a stable.

In this embodiment, the wires 28 and 29 connected to the two ends of the thin, electrically conducting wire 9 are connected through an extensible electric cable 60 to a control unit 61 fixed to the ceiling of the stable above the cow 4 as shown on FIG. 9. The alert device further comprises an alarm device 62 electrically connected to the control unit 61 through a pair of wires 63. The alarm device 62 comprises a buzzer 64 and a switch 65 provided as stated above to allow the attendant to stop the sound produced through the buzzer 64 after he has acknowledged the alarm. The wires 63 must be of a sufficient length to allow a remote position of the alarm device 62 with respect to the unit 61. This alarm device 62 may be for example located into the house of a farm and the wires 63 must in this case extend from the control unit 61 fixed to the ceiling of the stable above the cow 4 to the alarm device 62 located in the house.

As illustrated in FIG. 10, the control unit 61 may be supplied from an AC outlet in which a plug 66 is introduced. The current from the AC outlet is supplied to a step down to a low voltage transformer 67 and rectified through a full-wave rectifier 68. The positive and negative outputs of the full wave rectifier 68 supplies through the thin wire 9, the wires 28 and 29, and the cable 60 a coil 69 of an electromechanical relay 70 to position the movable contact 71 of the relay 70 as shown on FIG. 10. Upon breaking of the wire 9 caused by parturition of the cow 4, the coil 69 of the relay 70 is de-energized so that the movable contact 71 comes into contact with the contact 72. The positive and negative outputs of the rectifier 68 then energize the buzzer 64 of the alarm device 62 through the pair of wires 63, the normally closed contacts 71 and 72, and the switch 65 to thereby indicate to the attendant parturition of the cow. It should be noted that the relay 70 forms part of the device for detecting the onset of parturition of the animal as it detects breaking of the wire 9.

The embodiment of the alert device according to the present invention illustrated on FIGS. 9 and 10 is therefore simplified as it includes no transmitter-receiver tandem.

Of course, the alarm device 56 (FIG. 8) or 62 (FIGS. 9 and 10) may be replaced by a telephone set automatically operated through the receiver 52 (FIG. 8) or the relay 70 (FIG. 10) to warn the attendant about the onset of parturition of the cow 4.

It can be appreciated that any disconnection of the thin, electrically conducting wire 9 is signaled by the alarm device 56 (FIG. 8) or 62 (FIGS. 9 and 10) as when the wire 9 is broken. This permits to the attendant to take corrective measures.

It can also be appreciated that the alert device according to the present invention is completely reusable except for the thin, electrically conducting wire 9 and stoppers 14 and 15 which must be replaced at each parturition onset detection.

Moreover, the receiver 52 (FIG. 8) can possibly be supplied from an AC (alternating current) outlet when located at a fixed position, thereby eliminating the necessity of a design which reduces electric power consumption.

Although the present invention has been described in detail hereinabove by way of preferred embodiments thereof, it should be pointed out that any modification to these preferred embodiments or application to animals other than cows, within the scope of the appended claims, is not deemed to change the nature and scope of the present invention.

The embodiments of the invention in which an exclusive property or privilege is claimed are defined as follows:

1. A device for detecting the onset of parturition of a pregnant animal, comprising:
   a thin, electrically conducting wire passing through a first perforation point made through the skin of the animal on the left side of the animal's vulva region, and also passing through a second perforation point made through the skin of the animal on the right side of the animal's vulva region, said thin, electrically conducting wire comprising a middle wire portion defined between said first and second perforation points and lying substantially across the vaginal orifice of the animal, said thin wire also comprising a first end, a second end, a first end portion defined between said first end and said first perforation point, and a second end portion defined between said second end and said second perforation point;
   first stopper means fixedly mounted on the first end portion of said thin wire close to the first perforation point, and second stopper means fixedly mounted on the second end portion of said thin wire close to the second perforation point, said first and second stopper means defining a central portion of said thin, electrically conducting wire, which central portion includes said middle wire portion, and said first and second stopper means causing, upon separation of the left and right sides of the animal's vulva region at the onset of parturition of the animal, a tensile stress into said central portion of the thin, electrically conducting wire in order to break said thin wire central portion; and
   means for detecting breaking of said central portion of the thin, electrically conducting wire to thereby detect the onset of parturition of said animal.

2. A detecting device according to claim 1, wherein said thin, electrically conducting wire is an electrically insulated wire having a small diameter.

3. A detecting device according to claim 1, wherein said first and second stopper means each comprise a split lead element, at least one turn of said thin, electrically conducting wire being wound around said split lead element being crushed.

4. A detecting device according to claim 1, wherein said means for detecting breaking of said central portion of the thin wire comprises an electronic switch having a first electrode and a second electrode, said central portion of the thin, electrically conducting wire interconnecting said first and second electrodes whereby breaking of said thin wire central portion disconnects said first and second electrodes to allow said electronic switch to detect breaking of said central portion of the thin, electrically conducting wire.

5. A detecting device according to claim 1, in which said means for detecting breaking of said central portion of the thin wire comprises (a) an electromechanical relay having a coil and normally closed contacts, and (b) a low voltage electric source for supplying the coil of said electromechanical relay through said central portion of the thin, electrically conducting wire whereby breaking of said thin wire central portion de-energizes said coil to close the normally closed contacts, which closure of the normally closed contacts indicates breaking of said central portion of the thin, electrically conducting wire.

6. A detecting device according to claim 1, wherein said animal has two front legs and a tail, and wherein said detecting device further comprises:
   first strap means mounted on the back of the animal and including a first end and a second end; and
   second strap means surrounding the animal's body behind the two front legs of the animal;
   said first end of the first strap means being connected to said second strap means and said second end of the first strap means comprising a loop in which passes the tail of the animal whereby said first strap means is maintained in place on the back of the animal by said tail and said second strap means.

7. A detecting device according to claim 6, wherein said means for detecting breaking of said central portion of the thin wire is mounted on the first strap means adjacent the second strap means, and wherein said detecting device further comprises
   a pair of electrically conducting wires for interconnecting said means for detecting breaking of said central portion of said thin wire to the first and second end portions of the thin, electrically conducting wire, said pair of wires being mounted on the first strap means; and
   connector means for interconnecting the two wires of said pair to the first and second end portions of said thin wire, respectively.

8. A detecting device according to claim 6, wherein said first and second strap means include elastic portions and means for allowing adjustment of said first and second strap means on the animal.

9. A detecting device according to claim 6, further comprising a pair of electrically conducting wires attached to said first strap means, and connector means for interconnecting the two wires of said pair to the first and second end portions of said thin, electrically conducting wire, respectively.

10. A detecting device according to claim 9, wherein said means for detecting breaking of said central portion of the thin wire are positioned remote from said animal, said parturition detecting device further comprising an extensible electrical cable for interconnecting said pair of wires to said means for detecting breaking of said central portion of the thin, electrically conducting wire.

11. A parturition alert device comprising:
a parturition detecting device according to claim 1; and
means for producing an alarm indicating the onset of parturition of the animal in response to detection of breaking of said central portion of the thin, electrically conducting wire by said breaking detecting means of the parturition detecting device.

12. The alert device of claim 11, wherein said alarm producing means comprises a transmitter unit for transmitting a signal in response to detection of breaking of said central portion of the thin wire by said breaking detecting means, and a receiver unit for receiving said transmitted signal and for producing said alarm in response to said received signal.

13. The alert device of claim 12, wherein said alarm producing means further comprises an alarm generator energized by said receiver unit in response to said received signal to thereby produce said alarm.

14. The alert device of claim 13, wherein said alarm producing means comprises wires of substantial length for interconnecting said alarm generator with said receiver unit whereby said alarm generator can be positioned remote from said receiver unit and can still be energized by this receiver unit through said wires of substantial length to produce said alarm.

15. The alert device of claim 11, wherein said alarm producing means comprises sound generating means through which said alarm is produced and a manually operated switch for disconnecting said sound generating means.

16. The alert device of claim 11, wherein said alarm producing means comprises a buzzer to produce said alarm and an electrical source to supply said buzzer with electric energy, said breaking detecting means of the parturition detecting device comprising means for connecting said electrical source to said buzzer upon detection of breaking of said central portion of the thin, electrically conducting wire in order to energize said buzzer so as to produce said alarm.

17. The alert device of claim 16, wherein said breaking detecting means of the parturition detecting device comprises switching means interposed between said buzzer and said electrical source, and energized through said central portion of the thin electrically conducting wire, whereby breaking of said central portion of the thin wire de-energizes said switching means which then activate said buzzer by connecting it to said electrical source.

18. The alert device of claim 16, wherein said alarm producing means comprises wires of substantial length for interconnecting said electrical source with said buzzer whereby said buzzer can be positioned remote from said electrical source while it can still be energized by said electrical source through said wires of substantial length.

19. The alert device of claim 11, wherein said alarm producing means comprises means for producing said alarm at a location remote from said animal.

* * * * *